United States Patent [19]

Wu

[11] Patent Number: 4,847,436
[45] Date of Patent: Jul. 11, 1989

[54] DECOMPOSITION OF DIHYDROPEROXIDE TO RESORCINOL

[75] Inventor: Ching-Yong Wu, Pittsburgh, Pa.

[73] Assignee: Indspec Chemical Corporation, Pittsburgh, Pa.

[21] Appl. No.: 136,316

[22] Filed: Dec. 22, 1987

[51] Int. Cl.$^4$ ............................................. C07C 37/08
[52] U.S. Cl. .................................. 568/768; 568/763; 568/771
[58] Field of Search ................ 568/769, 768, 763, 771

[56] References Cited

U.S. PATENT DOCUMENTS

| | | | |
|---|---|---|---|
| 3,923,908 | 12/1975 | Suda et al. | 568/768 |
| 4,229,596 | 10/1980 | Burkholder et al. | 568/768 |
| 4,239,921 | 12/1980 | Hashimoto et al. | 568/768 |
| 4,339,615 | 7/1982 | Imai et al. | 568/768 |
| 4,463,199 | 7/1984 | Chiyodu et al. | 568/768 |

FOREIGN PATENT DOCUMENTS

| | | | |
|---|---|---|---|
| 7853626 | 5/1978 | Japan | 568/768 |
| 1455450 | 11/1976 | United Kingdom | 568/768 |
| 2071662 | 9/1979 | United Kingdom | 568/768 |

*Primary Examiner*—Werren B. Lone
*Attorney, Agent, or Firm*—Kirkpatrick & Lockhart

[57] ABSTRACT

An improvement in the preparation of resorcinol includes the decomposition of m-diisopropylbenzene dihydroperoxide (m-DHP) to resorcinol and acetone in the presence of an effective amount of a catalyst selected from the group consisting of boron trifluoride, ferric chloride and stannic chloride. Minute quantities of the catalyst, preferably 10 to 50 ppm, are effective to increase the yields of resorcinol.

3 Claims, 1 Drawing Sheet

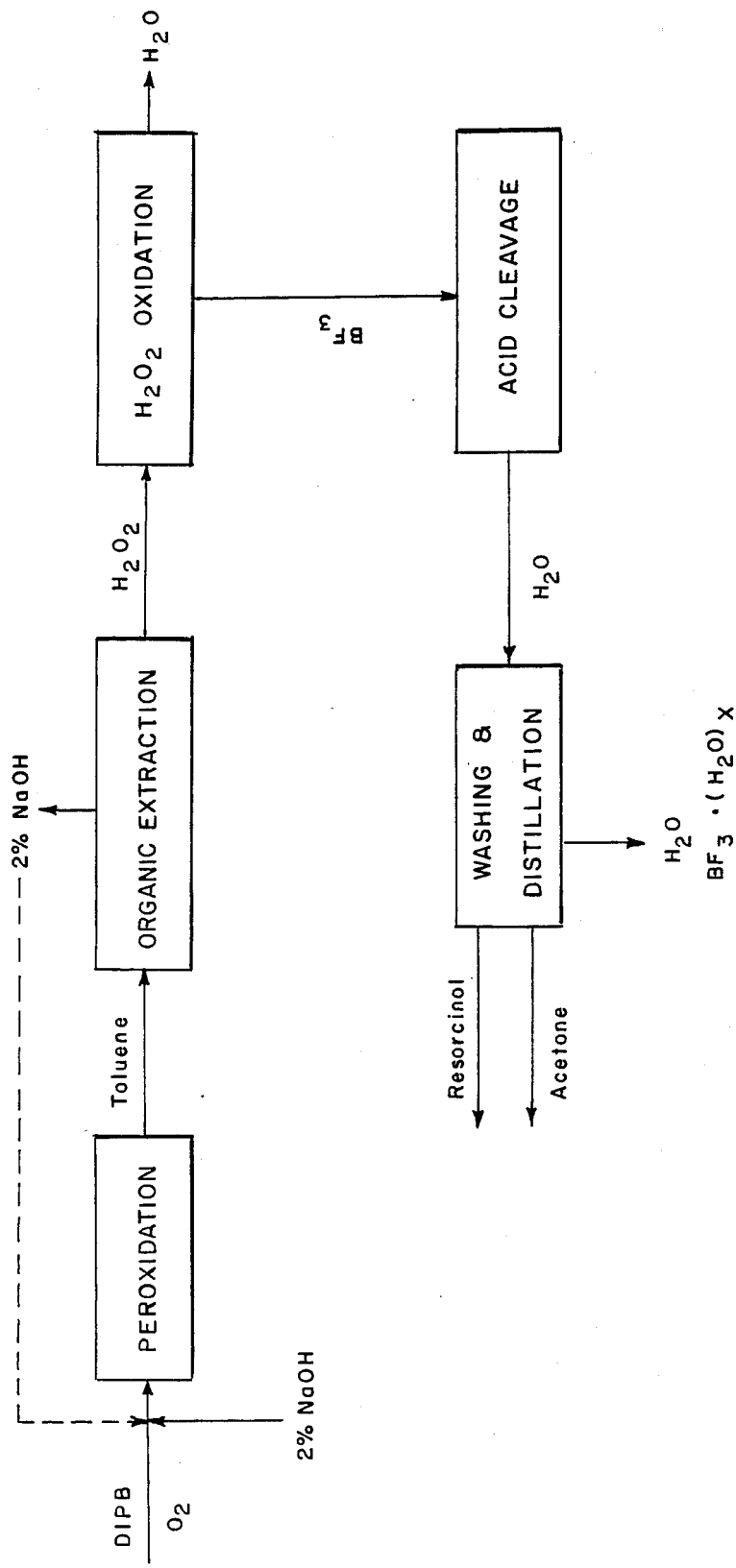

DECOMPOSITION OF DIHYDROPEROXIDE TO RESORCINOL

BACKGROUND OF THE INVENTION

1. Field of the Invention:

The present invention relates to a process for the decomposition of dihydroperoxide to resorcinol, and more particularly to the catalytic decomposition of m-diisopropylbenzene dihydroxide.

2. Description of the Prior Art:

In 1972, researchers at the Stanford Research Institute (SRI) reviewed a new route for the preparation of resorcinol via hydroperoxidation. The SRI process involves production of m-diisopropylbenzene (m-DIPB) by alkylation of benzene and/or cumene with propylene, followed by the oxidation of m-DIPB to diisopropylbenzene dihydroperoxide (m-DHP) and other by-products. The DHP is then decomposed to resorcinol and acetone with the aid of an acid catalyst.

Numerous methods have since been proposed to improve upon the preparation of resorcinol by the hydroperoxidation route.

The decomposition of m-DHP to resorcinol is usually carried out in the liquid phase, in a substantially anhydrous organic solvent, such as acetone, methyl isobutyl ketone (MIBK), benzene, or toluene. The decomposition is highly exothermic, and produces one mole of resorcinol and two moles of acetone from each mole of m-DHP. Small quantities of strong acids, for example sulfuric acid or orthophosphoric acid ($H_2SO_4$ and $H_3PO_4$, respectively), are used as catalyst.

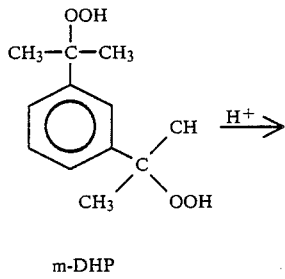

m-DHP

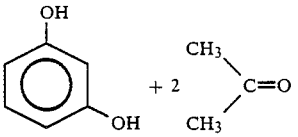

The rate of DHP decomposition is thought to be first order based on DHP; it is accelerated by acid and by resorcinol but retarded by water. All hydroperoxides present in the feed will be converted to acetone and corresponding phenolic products. Thus, other oxidation by-products such as m-monohydroperoxides (m-MHP) will form m-isopropylphenol and m-hydroxyhydroperoxides (m-HHP) will form m-(alpha-hydroxyisopropyl)phenol, which immediately dehydrates to m-isopropenylphenol.

According to the SRI review referenced above, the MIBK extract of m-DHP is evaporated to produce a 50% solution of hydroperoxides. Concentrated sulfuric acid (0.2 wt %), as catalyst, and 70% hydrogen peroxide (25% excess) to oxidize HHP and the dicarbinols (DCL), are added to this solution in a continuous reactor at 80° C. The addition rates are such that an eight minute residence time is achieved. After the cleavage, the sulfuric acid is neutralized with a slurry of hydrated lime and the solids are removed by filtration. The filtered cleavage product is distilled to remove acetone and MIBK. The aqueous distillation bottom is extracted with toluene to selectively remove impurities (isopropylphenol and heavy ends) from the aqueous resorcinol solution. The purified aqueous raffinate is evaporated to remove part of the water. The concentrated aqueous solution is allowed to grow crystals. Finally, the resorcinol is separated by centrifugation and dried.

However, according to British Patent Specification No. 1,455,450, published in 1976, only by using pure m-DHP for the acid-catalyzed decomposition can relatively pure resorcinol be obtained. When product from the hydroperoxidation of m-DIPB is directly used in the decomposition, the resulting reaction product contains, besides resorcinol and the compound produced from other hydroperoxides, a number of other secondary products formed by subsequent reactions of the decomposition components and products under the action of acid catalyst. Resorcinol and acetone react to form resins and resorcinol and isopropenylphenol react to give a high-boiling adduct. The isopropenylphenol also polymerizes to give both liquid and solid polymers. The chemistry involved when a DHP/HHP mixture is decomposed in the presence of acid-catalyst is presented below.

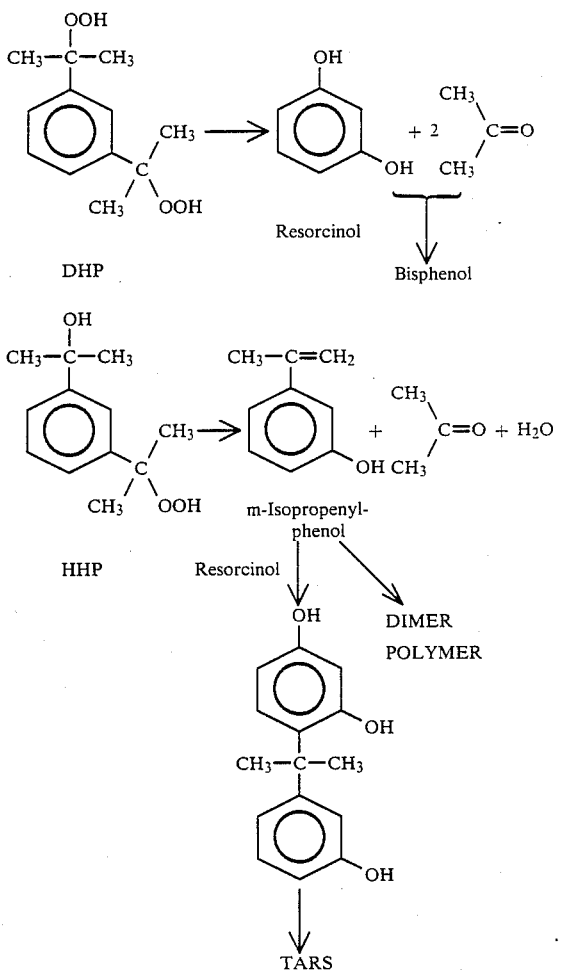

Similarly, Suda et al. U.S. Pat. No. 3,923,908 to Sumitomo Chemical Company discussed the relationship between DHP purity and the resorcinol yield from its decomposition. The yields of resorcinol are highly dependent on the amount of impurities containing the 2-hydroxy-2-propyl group, such as carbinols and HHP. Best results (90–95% yields) are obtained when the ratio of these groups to the number of molecules of DHP is below 0.16. In other words, the mol % HHP in the DHP/HHP sample can not be greater than 14%. A way to obtain such a high purity DHP/HHP sample is not mentioned in the patent.

Imai et al. U.S. Pat. No. 4,339,615 to Mitsui Petrochemical Industries discloses a process for producing resorcinol, which comprises cleaving pure m-DHP in the presence of a water-soluble acid catalyst (sulfuric acid in acetone) in a mixed solvent consisting of an aromatic hydrocarbon and acetone. An 86% resorcinol yield is reported using a DHP/HHP sample containing 3.9 mol % HHP. The pure DHP probably is obtained by treating their hydroperoxidation product with hydrogen peroxide.

British Patent Application No. GB 2 071 662 A discloses the use of superacid catalysts, such as boron trifluoride-hydrogen fluoride complex in the preparation of resorcinol from m-DIPB.

Many patents have disclosed procedures for the purification of crude resorcinol obtained by decomposing m-DHP with acid catalysts. For example, a Japanese patent, Japan Kokai No. 78-53626, issued to Sumitomo Chemical Company claims a simple distillation process to obtain pure resorcinol. Crude resorcinol from the DHP decomposition is distilled in vacuo at less than 210° C. pot temperature to effectively remove impurities produced in the acid-catalyzed decomposition.

Another patent, Hashimoto et al. U.S. Pat. No. 4,239,921, issued in 1980 to Mitsui Petrochemical Industries, discloses an improved resorcinol purification by solvent recrystallization. The patent claims that both low-boiling and high-boiling impurities can be removed from the crude resorcinol by a recrystallization process using a mixed solvent consisting of a specific ratio of an aromatic hydrocarbon, an alkylphenol, and an acylphenol. For example, the resorcinol recrystallized from a mixture of toluene-isopropylphenol has only 30 ppm of high boiling and 60 ppm of low boiling impurities.

An object of the present invention is to improve the yields of resorcinol obtained from the decomposition of m-DHP.

SUMMARY OF THE INVENTION

The object of the present invention is satisfied by an improvement in the decomposition of m-DHP. In a process for the preparation of resorcinol, the improvement includes decomposing m-DHP in the presence of an effective amount of a catalyst selected from the group consisting of boron trifluoride, ferric chloride and stannic chloride. The water content in the reaction solution should be less than about 0.1 wt %. When boron trifluoride is selected for the catalytic decomposition of m-DHP, the catalyst is present in an amount preferably within the range of about 10 to 100 ppm and more preferably, about 10 to 50 ppm. The catalyst is preferably neutralized following the decomposition step.

BRIEF DESCRIPTION OF THE FIGURE

The single FIGURE is a schematic illustration of the preferred embodiment of the process of the present invention.

DETAILED DESCRIPTION OF THE PREFERRED EMBODIMENTS

In the process of the present invention, shown schematically in the Figure, resorcinol is prepared by essentially a three step process. In the first step, diisopropylbenzene (DIPB) is oxidized with oxygen or air according to any suitable technique. Selected oxidation products, including m-DHP, are extracted in the second step. After any suitable further treatment to provide beneficial quantities of m-DHP, the m-DHP is decomposed in the third step to resorcinol and acetone in the presence of an effective amount of a catalyst selected from the group consisting of boron trifluoride, ferric chloride and stannic chloride. The resorcinol and acetone are then purified by any suitable process.

DECOMPOSITION OF M-DHP TO RESORCINOL

The last step of the 3-step hydroperoxidation process is the decomposition of m-DHP in the presence of acidic catalysts to co-produce resorcinol and acetone. In the current commercial process, this is done in the presence of a small amount, in the percent composition range, of a Bronsted acid catalyst, generally a mineral acid, such as sulfuric acid. The decomposition product, usually dissolved in an organic solvent, is neutralized with dilute alkali and then distilled to obtain crude resorcinol.

An improved method for the decomposition of m-DHP using a Lewis acid catalyst selected from the group consisting of boron trifluoride, ferric chloride and stannic chloride, preferably anhydrous boron trifluoride or its complexes, is provided by the present invention. From the results presented in Table I it is shown that the activity of the boron trifluoride catalyst is higher than the conventional catalysts. This is a definite advantage for using $BF_3$ in the decomposition of m-DHP. The decomposition of m-DHP has been achieved using significantly smaller amounts of catalyst, e.g. 10 to 100 ppm, and as low as 10 to 50 ppm, at a temperature of about 50° C.

EXAMPLE 1

In a 100 ml 3-neck flask equipped with a stirrer, thermometer, and reflux condenser was placed 15 g of m-DHP dissolved in 75 ml of MIBK (or toluene). The flask was heated in a water-bath maintained at 50° C. with stirring. Using a microliter syringe, 25 microliters of boron trifluoride etherate ($BF_3.Et_2O$) was charged to the flask to start the decomposition of m-DHP to resorcinol. After one hour of reaction, the reaction mixture was cooled to room temperature and a small sample was analyzed by GLC. The reaction mixture was immediately transferred to a Rinco evaporator and the solvent was evaporated at 40° C. and 4 mm pressure (higher pressure if toluene is used as solvent). The recovered solid was weighed and analyzed by HPLC. Resorcinol yield was calculated from the sample weight and resorcinol wt % in the HPLC analysis.

Table I shows the yields of resorcinol from the decomposition of m-DHP containing only a small percentage of m-HHP.

TABLE I

| | | | Amt. BF$_3$[2] | Resorcinol Yield, % | |
|---|---|---|---|---|---|
| Run | % m-DHP[1] | Solvent | μl. | by GLC | by HPLC |
| 1 | 95 | MIBK | 25 | 101.1 | 98.0 |
| 2 | 90 | Tol | 25 | 95.9 | 95.9 |
| 3 | 80 | MIBK | 30 | 85.3 | 84.3 |
| 4 | 70 | MIBK | 40 | 77.9 | 72.7 |
| 5 | 90 | Tol | 50[3] | 61.1 | ND[4] |

[1]Percent m-DHP from iodometric titration.
[2]BF$_3$ etherate.
[3]Ninety-six (96) % H$_2$SO$_4$ was used in this experiment.
[4]Not determined.

Analysis of the decomposition product, either by GLC or HPLC, indicates a high selectivity to resorcinol. In the prior art hydroperoxidation processes, it is difficult to obtain resorcinol in high purity. The advantage of using a boron trifluoride catalyst is evident. Even with less pure m-DHP (other components are m-HHP and m-MHP), resorcinol yields are still better than the decomposition of pure m-DHP (90%) with a sulfuric acid catalyst.

The m-DHP fraction must be dried prior to decomposition with boron trifluoride. It has been observed that the higher the moisture content, the greater amount of catalyst is required. Water decreases the activity of boron trifluoride by producing a less active catalytic species which favors the production of undesirable decomposition products. An approximate upper limit of water content has been determined to be 0.1 wt %.

EXAMPLE 2

In a 200 ml flask was placed 75 ml of solvent (toluene of MIBK) and 15 ml of an aqueous solution containing 6 M H$_2$O$_2$ and 1.5 M H$_2$SO$_4$. After stirring at room temperature for 30 min., the aqueous phase was separated and the solvent was dried with 5 g drying agent (anhydrous Na$_2$SO$_4$ or 4 A Molecular Sieves) at 50° C. for 30 min. The solvent was used to decompose 7.5 g of m-DHP (>90% purity) using as much BF$_3$-Et$_2$O catalyst as needed to start the decomposition of DHP at 50° C. After one hour of reaction, the reaction mixture was cooled to room temperature and the solvent was evaporated at 40° C. and 4 mm pressure using a Rinco evaporator. The recovered solid was weighed and analyzed by HPLC for resorcinol. Resorcinol yield was calculated from the sample weight and resorcinol wt. % in the HPLC analysis. The results are shown in Table II.

TABLE II

Effect of H$_2$O in Solvent on Resorcinol Yield

| Run | Solvent | Drying Agent | % H$_2$O in Solvent[1] | Amount BF$_3$—Et$_2$O used (ml) | Resorcinol yield, % |
|---|---|---|---|---|---|
| 1 | Toluene | none | 0.029 | 0.035 | 75 |
| 2 | Toluene | Na$_2$SO$_4$ | 0.024 | 0.030 | 78 |
| 3 | Toluene | 4A Sieves | 0.012 | 0.025 | 83 |
| 4 | MIBK | none | 2.5 | 0.20 | 52 |
| 5 | MIBK | Na$_2$SO$_4$ | 1.8 | 0.30 | 54 |
| 6 | MIBK | 4A Sieves | 0.065 | 0.030 | 80 |

[1]Determined by Karl Fisher method.

Table III summarizes the decomposition of m-DHP/m-HHP mixtures obtained directly from the caustic extraction of m-DIPB hydroperoxidation products. Yields of resorcinol based on m-DHP present were 2.7% to 33.7% lower than the theoretical yields. In general, when low purity m-DHP is decomposed, there is a lower resorcinol yield. This is not surprising because it usually takes 2 to 3 days to finish the work-up procedure, and resorcinol is a very reactive compound and probably forms secondary products, especially in the presence of an acidic catalyst.

TABLE III

Variation of Resorcinol Yield with m-DHP Purity

| Run | m-DHP Purity,[1] mol % | Product Purity, % Resorcinol | % Yield (on DHP) |
|---|---|---|---|
| 1 | 100 | 86.9 | 91.5 |
| 2 | 94 | 75.0 | 82.7 |
| 3 | 78 | 48.0 | 72.7 |
| 4 | 74 | 31.0 | 54.7 |
| 5 | 72 | 30.0 | 54.6 |
| 6 | 68 | 22.5 | 34.3 |
| 7 | 52 | 21.5 | 49.3 |

[1]Mol % m-DHP determined by HPLC.

EXAMPLE 3

The following procedure was used to obtain more accurate data for the decomposition of m-DHP/m-HHP mixture using a boron trifluoride catalyst.

In a 100 ml 3-neck flask equipped with a stirrer, thermometer, and reflux condensor was placed 7.5 g m-DHP/m-HHP mixture dissolved in 75 ml toluene. The flask was heated in a water-bath to 50° C. with stirring. After removing the water-bath, 15-100 microliters of boron trifluoride etherate was introduced below the liquid surface, using a microliter syringe and a long needle. The flask was cooled with an ice-water bath to remove the exothermic heat of reaction. The flask was maintained at 50° C. for 45 minutes and then cooled to room temperature. The contents were transferred to a 150 ml sep-funnel and 50 ml water was added. After shaking for a few minutes, a 10% aqueous sodium carbonate solution was added dropwise until the pH of the aqueous phase was neutral (pH=7). The toluene phase was separated and the aqueous phase was extracted three times with 50 ml portions of ether. The combined ether and toluene solutions were evaporated to dryness and the residue was weighed and analyzed by HPLC, using a standard technique for analysis of resorcinol.

Table IV shows the effect of catalyst neutralization (with 10% aqueous Na$_2$CO$_3$) on the yields of resorcinol using boron trifluoride as catalyst. It shows not only that the yields are increased by neutralizing the boron trifluoride catalyst immediately after the decomposition of m-DHP, but also that if acetone is used as solvent and boron trifluoride catalyst is not removed after the decomposition, there will be a large reduction in resorcinol yield indicating a possible reaction between resorcinol and acetone.

TABLE IV

Effect of Catalyst Neutralization on Resorcinol Yield

| Run | m-DHP,[1] % | Solvent | Product Purity, % Resorcinol | Yield, (on DHP) | % Catalyst Neutralization |
|---|---|---|---|---|---|
| 1 | 100 | Toluene | 86.9 | 91.5[2] | w/o neut. |
| 2 | 100 | Toluene | 85.5 | 85.5 | w neut. |
| 3 | 100 | Acetone | 65.5 | 75.0 | w/o neut. |
| 4 | 100 | Acetone | 90.0 | 90.1 | w neut. |
| 5 | 74 | Toluene | 21.5 | 36.9 | w/o neut. |
| 6 | 74 | Toluene | 29.0 | 50.3 | w neut. |
| 7 | 74 | Acetone | 10.5 | 19.9 | w/o neut. |
| 8 | 74 | Acetone | 44.5 | 72.6 | w neut. |

[1]% m-DHP was determined by HPLC.
[2]The lower yield with neutralization may be due to mechanial losses during the washing step.

In order to minimize uncertainties in resorcinol yield due to the loss of resorcinol during work-up of m-DHP decomposition products, the following GLC analysis method was used to obtain improved resorcinol yields. Results are shown in Table V.

EXAMPLE 4

The decomposition of 7.5 g m-DHP/m-HHP sample in 75 ml solvent with a small amount of boron trifluoride etherate was made using the same procedure as described. After the decomposition, the solution was cooled to room temperature with an ice-water bath. The product was transferred to a 250 ml volumetric flask and diluted to 250 ml with toluene. An external standard was prepared by dissolving a weighed quantity of pure resorcinol (usually 1–3.5 g) in approximately 10 ml acetone and then diluting it to 250 ml with toluene. The two solutions were analyzed by GLC using the response factor of the external standard to determine the weight % resorcinol. A 10'×⅛" SS column packed with 10% OV17 at 210° C. was used for GLC analysis.

TABLE V

Decomposition of m-DHP with $BF_3$ Catalyst

| Run | % DHP in Sample[1] | Solvent | Resorcinol Yield,[2] mol % (on DHP) |
|---|---|---|---|
| 1 | 100.0 | MIBK | 96.6 |
| 2 | 81.0 | MIBK | 82.1 |
| 3 | 79.4 | MIBK | 82.4 |
| 4 | 75.1 | MIBK | 74.4 |
| 5 | 70.0 | MIBK | 70.4 |
| 6 | 54.1 | MIBK | 76.6 |
| 7 | 100.0 | Toluene | 96.4 |
| 8 | 67.5 | Toluene | 77.4 |
| 9 | 68.9 | Toluene | 76.9 |
| 10 | 67.4 | Toluene | 85.0 |

[1]Percent DHP was determined by HPLC analysis. Its accuracy was estimated to be ±2%.
[2]Based on GLC analysis.

Compared to currently available technology, the results of m-DHP decomposition catalyzed by boron trifluoride (See Table V) are excellent. The % resorcinol yields based on % DHP present in the sample are 70.4% to 96.6% depending on the purity of m-DHP. The yields are still higher when toluene is used as solvent, indicating a possible reaction between resorcinol and MIBK. These yields, however, are higher than those when concentrated sulfuric acid is used as catalyst. Run 5 of Table I gave a 61.1% resorcinol yield when 50 microliters of 96% sulfuric acid was used as catalyst, compared to a 95.9% yield when 25 microliter of boron trifluoride was used.

For comparison, decomposition of m-DHP in the presence of several different Lewis acid catalysts was investigated and the results are show in Table VI. Both boron trifluoride ($BF_3$) and stannic chloride ($SnCl_4$) gave the best yields. Ferric chloride ($FeCl_3$) also gave an acceptable yield. Boron trifluoride is, however, preferred in view of the potential environmental problems associated with stannic chloride. Decomposition with aluminum chloride ($AlCl_3$) gave a very poor yield of resorcinol. Therefore, not all Lewis acids are good catalysts for the decomposition of m-DHP.

TABLE VI

Evaluation of Lewis Acids for m-DHP Decomposition

| Run | DHP, Purity % | Solvent | Catalyst Type | Catalyst Amount | Resorcinol Yield, % (on DHP) |
|---|---|---|---|---|---|
| 1 | 100 | Toluene | $BF_3$[2] | 20 μl | 96.5 |
| 2 | 100 | Toluene | $SnCl_4$ | 25 μl | 100.6 |
| 3 | 100 | Toluene | $FeCl_3$ | 0.05 g | 86.7 |
| 4 | 100 | Toluene | $AlCl_3$ | 0.5 g | 14.0 |
| 5 | 100 | Toluene | $SO_3$ | 1 | 88.0 |
| 6 | 81 | MIBK | $BF_3$[2] | 170 μl | 82.1 |
| 7 | 81 | Toluene | $SnCl_4$ | 100 μl | 79.0 |

[1]Used 3.8 g of a 0.7% $SO_3$ in acetone.
[2]$BF_3$ etherate.

Another advantage of the boron trifluoride catalyst is its low activity in promoting the secondary reactions of the resorcinol that is produced. A minute quantity of boron trifluoride used to decompose m-DHP is not sufficient to promote the reaction between resorcinol and isopropenylphenol, for example. In addition, the boron trifluoride catalyst can readily be removed from the organic phase by washing with a small amount of aqueous sodium hydroxide. Thus, the crude resorcinol obtained by the boron trifluoride-catalyzed decomposition of m-DHP does not require a specific purification process. This is considered to be an advantage of the boron trifluoride-catalyzed decomposition of m-DHP provided by the process of the present invention.

What is claimed is:

1. In a process for the preparation of resorcinol, the improvement comprising:
    decomposing a solution of anhydrous m-diisopropylbenzene dihydroperoxide in the presence of an effective amount of a catalyst selected from the group consisting of boron trifluoride, ferric chloride and stannic chloride wherein the water content of said solution is less than about 0.1 wt%.

2. The improvement of claim 1 wherein said catalyst is boron trifluoride etherate and said effective amount is in the range of about 10 to 100 ppm.

3. The improvement of claim 1 wherein said catalyst is neutralized following the decomposition of m-diisopropylbenzene dihydroperoxide.

* * * * *